(12) United States Patent
Jackson

(10) Patent No.: US 8,475,501 B2
(45) Date of Patent: Jul. 2, 2013

(54) POLYAXIAL BONE SCREW WITH SPLIT RETAINER RING

(76) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 13/507,824

(22) Filed: Jul. 31, 2012

(65) Prior Publication Data

US 2012/0310291 A1 Dec. 6, 2012

Related U.S. Application Data

(63) Continuation of application No. 12/011,048, filed on Jan. 24, 2008, now Pat. No. 8,241,333, which is a continuation of application No. 10/650,910, filed on Aug. 28, 2003, now Pat. No. 7,322,981.

(51) Int. Cl.
*A61B 17/70* (2006.01)

(52) U.S. Cl.
USPC .................................................. 606/269

(58) Field of Classification Search
USPC .................... 606/246–279, 301–321
See application file for complete search history.

(56) References Cited

U.S. PATENT DOCUMENTS

| | | | |
|---|---|---|---|
| 5,312,404 A | 5/1994 | Asher et al. | |
| 5,429,639 A | 7/1995 | Judet | |
| 5,443,467 A | 8/1995 | Biedermann et al. | |
| 5,466,237 A * | 11/1995 | Byrd et al. | 606/272 |
| 5,476,464 A | 12/1995 | Metz-Stavenhagen et al. | |
| 5,501,684 A * | 3/1996 | Schlapfer et al. | 606/301 |
| 5,591,166 A * | 1/1997 | Bernhardt et al. | 606/266 |
| 5,601,553 A | 2/1997 | Trebing et al. | |
| 5,647,873 A * | 7/1997 | Errico et al. | 606/264 |
| 5,669,911 A * | 9/1997 | Errico et al. | 606/264 |
| 5,672,176 A | 9/1997 | Biedermann et al. | |
| 5,725,528 A | 3/1998 | Errico et al. | |
| 5,733,286 A | 3/1998 | Errico et al. | |
| 5,800,435 A | 9/1998 | Errico et al. | |
| 5,817,094 A | 10/1998 | Errico et al. | |
| 5,879,350 A * | 3/1999 | Sherman et al. | 606/270 |
| 5,882,350 A * | 3/1999 | Ralph et al. | 606/278 |

(Continued)

FOREIGN PATENT DOCUMENTS

| | | |
|---|---|---|
| DE | 19507141 | 9/1996 |
| EP | 1121902 | 8/2001 |
| GB | 9202745.8 | 4/1992 |

OTHER PUBLICATIONS

*EBI Omega 21* Brochure, EBI Spine Systems, pub. 1999.

(Continued)

*Primary Examiner* — Mary Hoffman
(74) *Attorney, Agent, or Firm* — John C. McMahon

(57) ABSTRACT

A polyaxial bone screw includes a head member and a shank member. The shank has a capture end and an opposite threaded end for threaded insertion into a vertebra. The head has a U-shaped cradle for receiving a spinal fixation rod and a central bore for receiving the capture end of the shank. An expandible retainer ring with a radial split is snapped onto the capture end of the shank to retain it within the head. The retainer ring has a spherical outer surface which forms a ball joint with a spherical socket cavity within the head to enable the head to be angled relative to the shank. A threaded closure plug is tightened within the cradle to clamp the rod into engagement with a knurled dome on the capture end of the shank to secure the rod relative to the vertebra.

13 Claims, 3 Drawing Sheets

U.S. PATENT DOCUMENTS

| | | | |
|---|---|---|---|
| 5,891,145 A * | 4/1999 | Morrison et al. | 606/266 |
| 5,938,663 A | 8/1999 | Petreto | |
| 6,019,759 A | 2/2000 | Rogozinski | |
| 6,063,090 A * | 5/2000 | Schlapfer | 606/270 |
| 6,074,391 A | 6/2000 | Metz-Stavenhagen et al. | |
| 6,077,262 A | 6/2000 | Schlapfer et al. | |
| 6,090,111 A | 7/2000 | Nichols | |
| 6,113,601 A * | 9/2000 | Tatar | 606/266 |
| 6,132,432 A | 10/2000 | Richelsoph | |
| 6,146,383 A | 11/2000 | Studer et al. | |
| 6,187,005 B1 * | 2/2001 | Brace et al. | 606/264 |
| RE37,161 E | 5/2001 | Michelson et al. | |
| 6,224,596 B1 | 5/2001 | Jackson | |
| 6,254,602 B1 | 7/2001 | Justis | |
| 6,273,888 B1 | 8/2001 | Justis | |
| 6,280,442 B1 * | 8/2001 | Barker et al. | 606/60 |
| 6,287,308 B1 | 9/2001 | Betz et al. | |
| 6,287,311 B1 | 9/2001 | Sherman et al. | |
| 6,302,888 B1 | 10/2001 | Mellinger et al. | |
| 6,355,040 B1 | 3/2002 | Richelsoph et al. | |
| 6,835,196 B2 | 12/2004 | Biedermann et al. | |
| 6,896,677 B1 | 5/2005 | Lin | |
| 7,322,981 B2 | 1/2008 | Jackson | |
| 7,445,627 B2 * | 11/2008 | Hawkes et al. | 606/269 |
| 7,682,377 B2 | 3/2010 | Konieczynski et al. | |
| 8,162,990 B2 * | 4/2012 | Potash et al. | 606/266 |
| 2001/0001119 A1 | 5/2001 | Lombardo | |
| 2003/0153911 A1 | 8/2003 | Shluzas | |
| 2005/0203516 A1 * | 9/2005 | Biedermann et al. | 606/61 |
| 2005/0216003 A1 * | 9/2005 | Biedermann et al. | 606/61 |
| 2006/0189984 A1 * | 8/2006 | Fallin et al. | 606/61 |
| 2007/0118123 A1 * | 5/2007 | Strausbaugh et al. | 606/61 |

OTHER PUBLICATIONS

*Claris Instrumentation* Brochure, G Med, pub. 1997.

*VLS System Variable Locking Screw* Brochure, Interpore Cross International, 1999.

*CD Horizon M8 Multi Axial Screw Spinal System* Brochure, Medtronic Sofamor Danek, no publish date.

*Contour Spinal System* Brochure, Ortho Development, no publish date.

*Xia Spinal System* Brochure, Stryker Howmedica Osteonics, no publish date.

*The Rod Plate System* Brochure, Stryker Howmedica Osteonics, pub. Oct. 1999.

*Silhouette Spinal Fixation System* Brochure, Sulzer Medica Spine-Tech, no publish date.

*SDRS Surgical Dynamics Rod System* Brochure, Surgical Dynamics, pub. 1998-1999.

*Versalok Low Back Fixation System* Brochure, Wright Medical Technology, Inc., pub. 1997.

*The Strength of Innovation* Advertisement, Blackstone Medical Inc., no publish date.

*The Moss Miami 6.0mm System* Advertisement, author unknown, no publish date.

\* cited by examiner

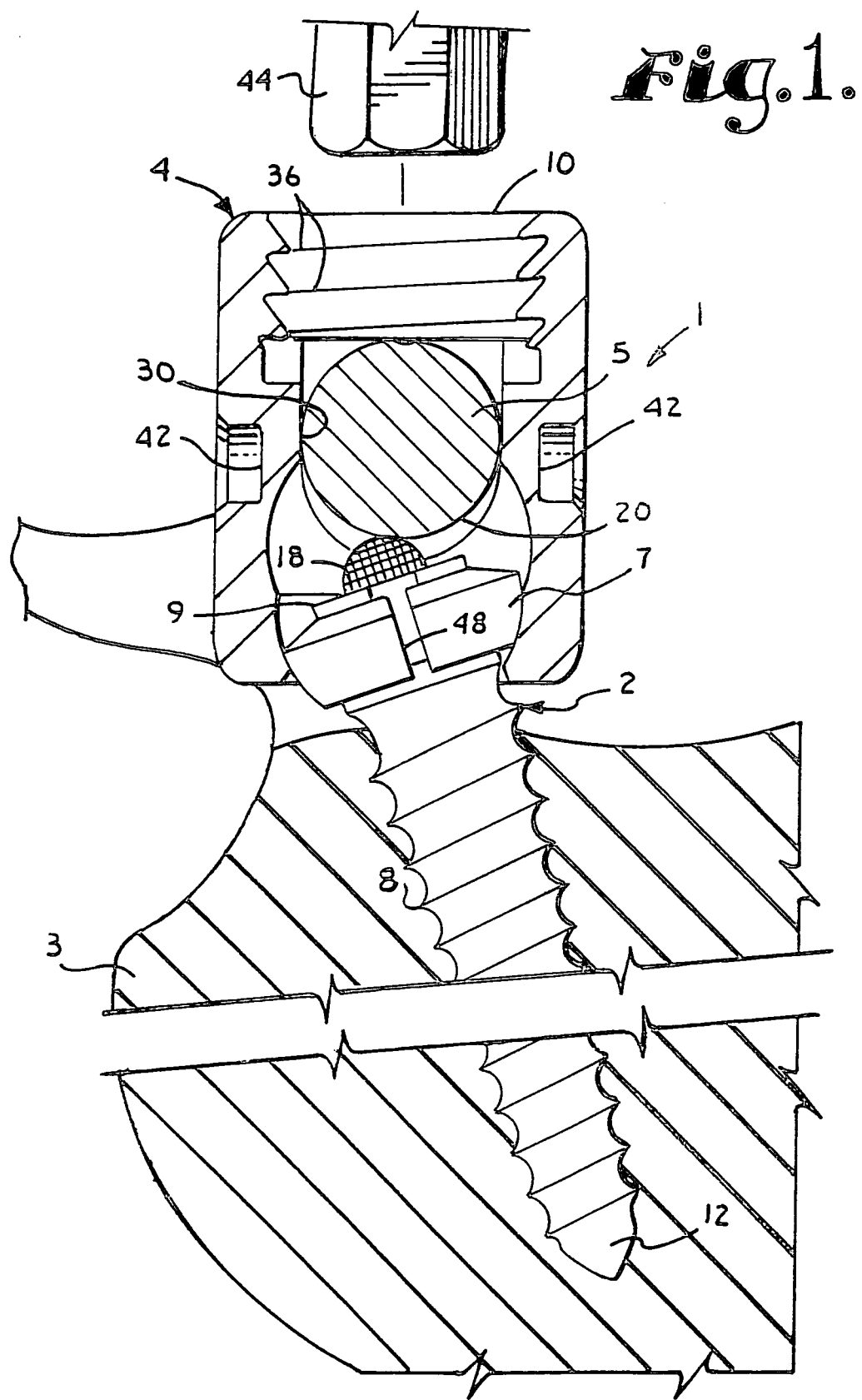

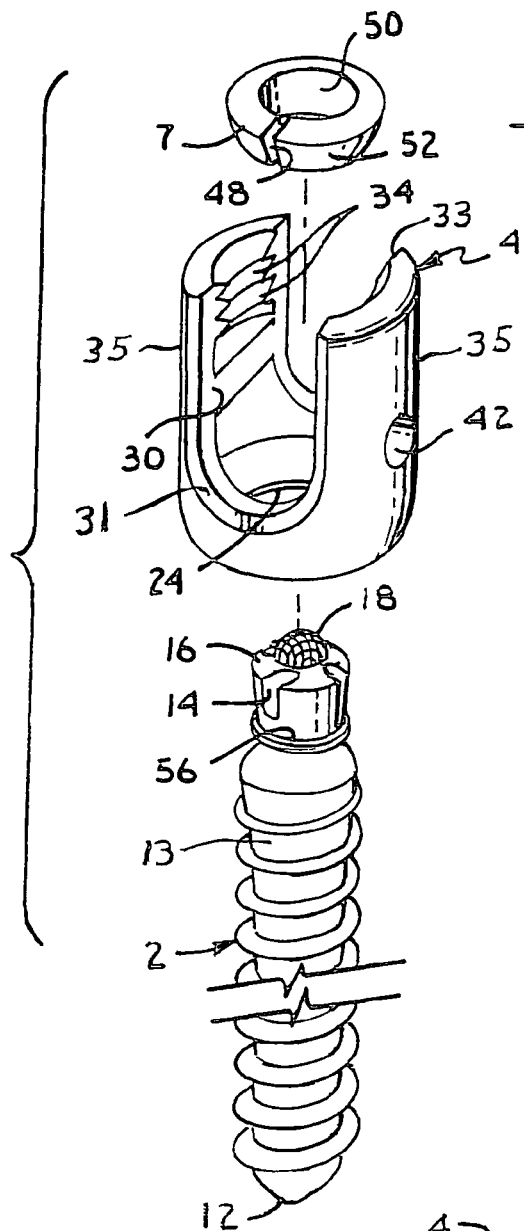
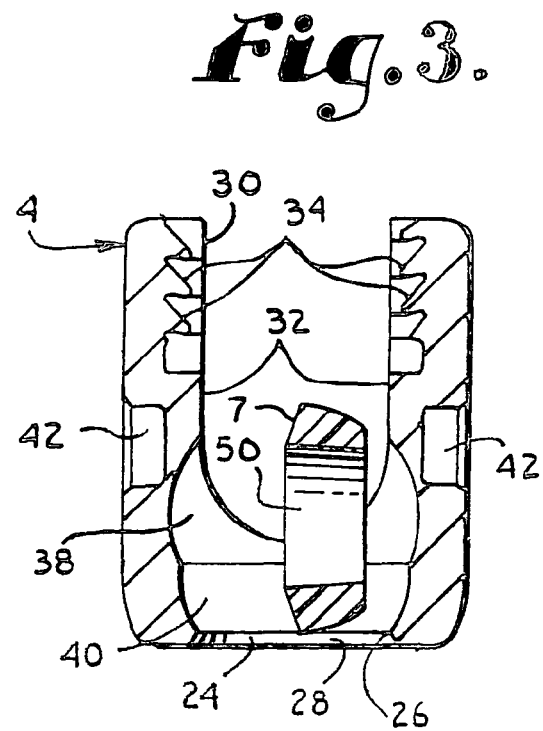
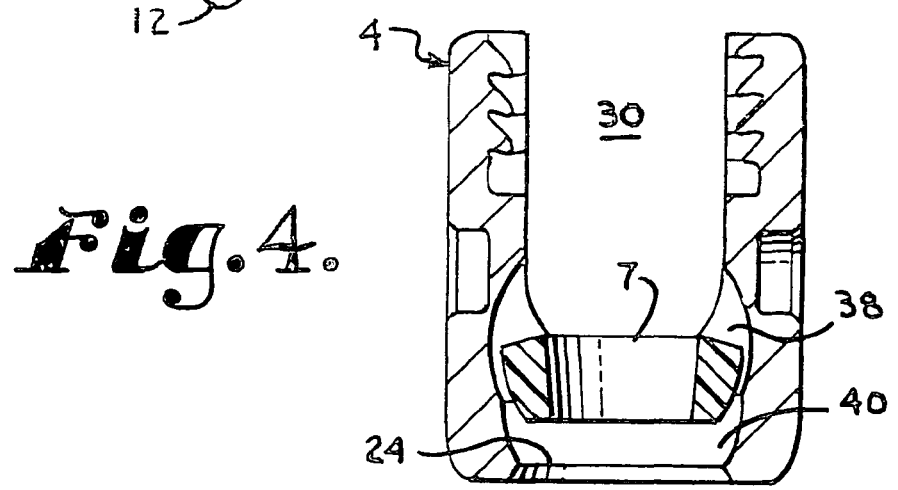

POLYAXIAL BONE SCREW WITH SPLIT RETAINER RING

CROSS REFERENCE TO RELATED APPLICATIONS

This application is a Continuation of U.S. patent Ser. No. 12/011,048, filed Jan. 24, 2009 that was a Continuation of U.S. patent Ser. No. 10/650,910, filed Aug. 28, 2003, the disclosures of which are incorporated by reference herein.

BACKGROUND OF THE INVENTION

The present invention is directed to a bone screw of the type wherein a head of the bone screw is swingable or can swivel about the shank of the bone screw until the surgeon is satisfied with the relative placement of the two parts and thereafter the head can be locked in position relative to the shank. Such screws are also referred to as polyaxial head or swivel head bone screws, since the head can be positioned in any of a number of angular configurations relative to the shank.

Bone screws are advantageously utilized in many types of spinal surgery in order to secure various implants to vertebrae along the spinal column. Bone screws of this type typically have a shank that is threaded and adapted to be implanted into a vertebral body of a vertebra. The bone screw includes a head which is designed to extend beyond the vertebra and which has a channel to receive another implant. Typically the channel will receive a rod or a rod-like member. In bone screws of this type, the head may be open, in which case a closure must be used to close between opposite sides of the head once a rod-like implant is placed therein, or closed wherein a rod-like implant passes through the head of a bone screw. Open head screws are most often used, mainly because it is difficult to feed long rods through closed head screws.

Bone screws are also available with heads permanently fixed relative to a shank or with polyaxial heads that initially swivel to allow placement and are then lockable in a desired positional configuration. When the head and shank of the bone screw are fixed in position relative to each other, it is not always possible to insert a bone screw into the bone in such a manner that the head will be in the best position for receiving other implants. Consequently, the polyaxial head bone screws have been designed that allow the head of the bone screw to rotate or swivel about an upper end of the shank of the bone screw, while the surgeon is positioning other implants and finding the best position for the bone screw head. However, once the surgeon has determined that the head is in the best position, it is then necessary to lock or fix the head relative to the shank. Different types of structures have been previously developed for this purpose. Unfortunately, the prior art devices have a tendency to be bulky, slip under high loading or require many parts.

It is desirable to have a polyaxial head bone screw that can be captured by the shank prior to locking of the head, but that allows the head to freely swivel or pivot about a top of the shank prior to locking. It is then further desirable to have the head capable of being fixably locked in a configuration or position relative to the shank where the head best fits with other elements of the overall spinal implant.

As noted above, many prior art swivel type bone screws have a bulky and heavy structure. In spinal surgery, it is desirable to provide a light weight implant that impacts on the surrounding tissue as little as possible. Consequently, it is desirable to have a bone screw with a low profile with respect to both height and width. It is also preferable to limit the width profile of the bone screw to provide more room to work along a rod or other implant in which many elements may be required in a relatively small space.

Furthermore, it is desirable to maintain the number of parts of the device at a minimum. Also, it is desirable to secure the various parts together in such a way, so that, if parts become loose under use for some reason, the device will not totally disassemble.

SUMMARY OF THE INVENTION

The present invention provides an improved polyaxial head bone screw assembly for use in conjunction with spinal surgery and, in particular, for implanting into a bone and securing other medical implants to the bone. The polyaxial bone screw assembly includes a threaded shank member for threaded placement in a bone, a head member connecting to another implant such as a spinal fixation rod and capturing a capture end of the shank member, and a retainer ring to capture and retain the capture end of the shank member within the head member. The shank member and head member may be set in a plurality of angular relationships with respect to each other within a range of obtuse angles.

The shank or shank member has an outer portion which is threaded, sized and shaped so as to be adapted to be operably screwed into a vertebral body in the spine of a patient. An end of the shank opposite the threaded lower portion includes a frusto-conical capture structure which diverges in diameter in a direction away from the threaded end of the shank. A top of the conical capture end is provided with apertures or formations for non-slip engagement by an installation tool to enable the shank to be threaded into a bone, such as a vertebra. Beyond the conical structure, a knurled dome is provided for positive interfering or cutting engagement by the surface of a rod which is to be clamped and supported by the bone screw assembly.

The head member is generally partially cylindrical in outer shape and has a central axial bore to receive the capture end of the threaded shank and a central U-shaped cradle opens in a direction opposite the axial bore to receive a spinal fixation rod and presents a pair of spaced apart arms. An interior of each of the arms includes threads to receive a threaded plug to secure the rod within the cradle and to clamp the rod into engagement with the knurled dome of the shank to fix the angular position of the head with respect to the shank. The head includes a lower partially spherical socket or seat at the lower end of the axial bore for receiving the ring and forms a neck for surrounding the shank during usage.

The retainer ring has an outer surface which is partially spherical and which is sized and shaped to fit within and swivel within the seat until locked in position, as noted below. The ring also has a central bore which is frusto-conical and of a shape which is compatible with the capture end of the shank to snugly receive the shank therein. The ring is sized to be too large in width to fit through the neck at the bottom of the head when in operable position and is either loaded from the top of the head or through other structure formed in the head. The ring is resiliently expandable to enable the ring to be snapped over the capture end of the shank to retain the capture end within the head member. The head has an assembly or orientation cavity therein which communicates with the U-shaped cradle and which is positioned and sized to enable proper orientation of the retainer ring and engagement of it with the capture end of the shank. The assembly cavity is spaced axially above the seat and neck and has a slightly larger partial spherical diameter than the seat so as to allow the ring to expand during insertion of the shank capture end and then return to a smaller diameter for snugly fitting in the seat. The spherical seat initially forms a pivot bearing with the retainer ring, when no axial downward force is applied to the shank and ring, to retain the capture end of the shank within the head and to enable pivoting the shank relative to the head throughout a limited range. The retainer ring is formed of a resilient or springy material and in a preferred embodiment has a radial split to enable expansion of the diameter of the ring and, particularly, to enable expansion of the diameter of the central bore to enable placement on the conical capture end of the shank.

Once the ring is on the shank and located in the seat in a position suitable to the surgeon with a rod received in the head channel, a closure plug is screwed into the threads between the arms so as to engage the rod and urge the rod under pressure into engagement with the dome on the shank. This in turn urges the spherical surface on the ring into frictional engagement with the spherical surface of the seat so as to lock the rotational position of the shank relative to the head. The dome of the shank is preferably radiused so that it engages the rod in the same manner no matter what alignment is formed between the head and the shank. The dome also preferably has a radius that is substantially less than the radius of the partial spherical surface of the ring. This reduces the required height of the head in comparison to the dome that is a continuation of the spherical surface.

Preferably, the shank feeds into the head from below through the neck of the head and has a smaller diameter in the region of the capture end than the diameter of the threads. This allows the shank to have a comparatively wide and normal thread for screwing into the bone that may be wider than the neck of the head, while also allowing the top of the shank to pass through the neck of the head to connect with the retainer ring.

Objects and Advantages of the Invention

Therefore, the objects of the present invention include: providing an improved bone screw assembly for implantation into a vertebra of a patient wherein the head of the bone screw is swingable or swivelable about an end of a shank of the bone screw until a desired configuration is obtained after which the head is lockable in position relative to the shank; providing such a screw assembly including a threaded shank with a capture end, a head member with a shank receiving bore and a U-shaped rod cradle for receiving a spinal fixation rod, a resiliently expandable shank retainer ring to retain the capture end of the shank within the head, and a threaded plug receivable in the head to engage a cradled rod and urge it into securing engagement with the capture end of the shank to fix the angular position of the shank relative to the head; providing such a screw assembly wherein the head member includes an internal partial spherical cavity, socket or seat and the retainer ring includes a partial spherical outer surface to enable swiveling and universal positioning of the shank relative to the head member from side to side and front to rear within a limited range; providing such a screw assembly in which the head member includes an assembly or orientation cavity above the seat to enable expansion of the ring during joining with the shank and proper orientation of the retainer ring; providing such a screw assembly in which the retainer ring has a radial split to enable resilient expansion and retraction of the ring for snapping the ring onto the capture end of the shank; providing such a screw assembly in which the capture end of the shank is frusto-conical, diverging in diameter in a direction away from the threaded part of the shank and in which the retainer ring has a central bore which is compatibly frusto-conical in shape; providing such a screw assembly in which the capture end of the shank has a knurled dome for positive, interfering engagement by a spinal fixation rod clamped within the assembly and wherein the dome has a radius that is smaller than the radius of the ring partial spherical surface; and providing such a polyaxial head bone screw which is economical to manufacture, which is convenient and secure in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged cross sectional view of a polyaxial head screw with a split retainer ring which embodies the present invention, shown assembled with a rod to hold the rod and inserted in a vertebral bone.

FIG. 2 is an exploded perspective view of elements of the bone screw at a reduced scale and illustrates a threaded shank member, a head member, and a retainer ring.

FIG. 3 is an enlarged cross sectional view of the screw head and illustrates the orientation of the split retainer ring for insertion into the head.

FIG. 4 is a view of the screw head similar to FIG. 3 and shows the orientation of the retainer ring to prepare for insertion of a capture end of a threaded shank.

DETAILED DESCRIPTION OF THE INVENTION

Figure 5:
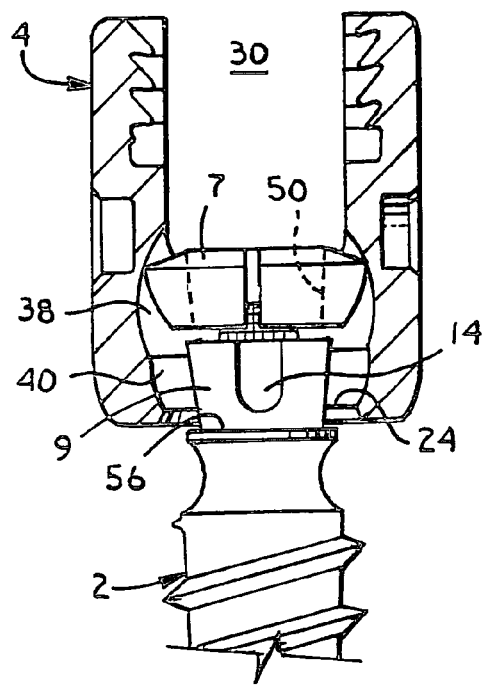
FIG. 5 is a view similar to FIG. 3 and shows the retainer ring about to be snapped onto the capture end of the threaded shank.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a polyaxial bone screw arrangement which embodies the present invention. The arrangement 1 includes a threaded shank member 2 for threadably implanting into a bone 3, such as a vertebra, and a head member 4 which connects with the shank member 2 to engage and secure a rod member 5, such as a spinal fixation rod, relative to the bone 3. The arrangement 1 also includes a retainer ring 7 operably positioned within head 4 and engaging a capture end 9 of the shank 2 opposite a region having a thread 8 to retain the capture end 9 within the head 4. The arrangement 1 further includes a plug or closure member 10 which urges the rod 5 into engagement with the capture end 9 of the shank 2. The head 4 and shank 2 cooperate in such a manner that the head 4 and shank 2 can be secured at any of a plurality of obtuse angles, relative to one another and within a selected range of angles both side to side and front to rear, to enable flexible engagement of the arrangement 1 with a rod 5.

Referring to FIGS. 1, 2, and 5, the shank 2 is elongated and is sized and shaped to be screwed into one of the vertebra 3. The shank 2 includes the external helically wound thread 8 that extends from an outer tip 12 to near the capture end 9. On the illustrated shank 2, the capture end 9 includes a region that is frusto-conical in shape, diverging in diameter in a direction away from the outer tip 12 and that is coaxially aligned with an axis of the shank 2. The illustrated capture end 9 has a maximum radius that is substantially less than a radius associated with the shank thread 8 and further, preferably less than the radius of a body 13 of the shank 2 in the region whereupon the thread 8 is located.

The capture end 9 has a plurality of tool engageable grooves, apertures or the like 14 to enable positive engagement by an appropriately shaped installation tool (not shown) to thread and drive the shank 2 into the vertebra 3. An upper end surface 16 of the capture end 9 opposite the tip 12 is provided with a formation or dome 18 to be positively and interferingly engaged by the rod 5 when the assembly 1 is assembled into place. The illustrated shank 2 includes the dome 18 which is radiused and knurled and that centered on the upper end surface 16 of the shank capture end 9 so as to be coaxial with the remainder of the shank 2. The scoring or knurling of the dome 18 operably frictionally abuts against a cylindrical surface 20 of the rod 5, when the plug 10 is tightened to provide non-slip engagement of the shank 2 relative to the rod 5 and to thereby help maintain a desired angular relationship between the shank 2 and the head 4. In certain embodiments, the purpose of the dome 18 is simply to be engaged by the rod 5 during assembly and pushed in such a manner as to frictionally engage the ring 7 with the head 4 as described below. Preferably, the dome 18 is radiused so that the dome 18 engages the rod at the same location even as the head 4 is swivelled relative to the shank 2. However, in certain embodiments the dome 18 could have other shapes.

Referring to FIGS. 2-8, the head member 4 is generally cylindrical in external profile and has a central and axially aligned shank receiving bore 24 ending at an inner and lower neck 26. The neck 26 is radiused to receive the shank capture end 9 and preferably smaller than the radius of the shank body 13 and thread 8. The bore 24 is also preferably sized larger than the capture end 9 of the shank 2 to enable the shank 2 to be oriented through a range of angular dispositions relative to the head 4. The bore 24 may be conically counterbored or beveled in a region 28 to widen the angular range of the shank 2.

The head 4 is provided with a U-shaped rod cradle 30 which is sized to receive the rod 5 therethrough. The illustrated cradle 30 is rounded and radiused at an inner or lower portion 31 to snugly mate with the surface of the rod 5 and open at an outer end 33, with spaced apart parallel side surfaces 32 so as to form upstanding and spaced apart arms 35 with inwardly facing threading thereon. The side surfaces 32 have mating and guide structures 34 formed thereinto which are complementary to mating and guide structures 36 of the closure plug 10 (FIG. 1). The structures 34 and 36 may be helically wound flanges or threads which advance the plug 10 into the head 4, as the plug 10 is rotated about its axis. It is foreseen that structures 34 and 36 may be V-shaped threads, buttress threads, reverse angle threads, or other types of threads or flange forms. Preferably, the structures 34 and 36 are of such a nature as to resist splaying of the arms 35 when the plug 10 is advanced into the cradle 30.

As seen in FIGS. 3 and 4, the head 4 has an assembly cavity 38 formed therein which opens into the cradle 30. A partially spherical socket or seat 40 communicates between the assembly cavity 38 and the shank bore 24 and has a radius that is slightly less than the radius of the assembly cavity 38 that is located axially directly thereabove. The purposes for the cavity 38 and seat 40 will be detailed further below. The head 4 may include external, closed end grip bores 42 for positive engagement by a holding tool (not shown) to facilitate secure gripping of the head 4 during assembly of the arrangement 1. The seat 40 has a spherical radius and extends upward coaxially through the head 4 from the neck 26 to the cavity 38.

The closure plug 10 is generally cylindrical in shape and is provided with a break-off head 44 which is connected to the plug 10 by a weakened area such that the head 44 separates from the plug 10 at a predetermined torque applied to the head 44 during assembly. The illustrated break-off head 44 has a hexagonal cross section for engagement by a tool (not shown) of a complementary shape.

The retainer ring 7 is used to retain the capture end 9 of the shank member 2 within the head member 4. The retainer ring 7 resiliently expands and contracts to enable the ring 7 to be snapped over and seated on the capture end 9 of the shank 2. The ring 7, like the remainder of the arrangement 1, is preferably formed of a material such as a spring stainless steel, tantalum, titanium or other resilient implantable material. The illustrated ring 7 has a radial split 48 which allows the ring 7 to expand in circumference to fit over the capture end 9. Alternatively, other configurations of the ring 7 are envisioned to enable such expansion and retraction of the ring 7. The ring 7 has a central conical bore 50 which is conically shaped to be compatible with the conical shape of the capture end 9. The ring 7 has an outer surface 52 which is frusto-spherical, partially spherical, or a segment of a sphere, and which has a spherical radius approximately equivalent to the spherical radius of the spherical seat 40 within the head 4 and smaller than the radius of the cavity 38. The ring surface 52 also has a radius substantially greater than the dome 18.

Figure 6:
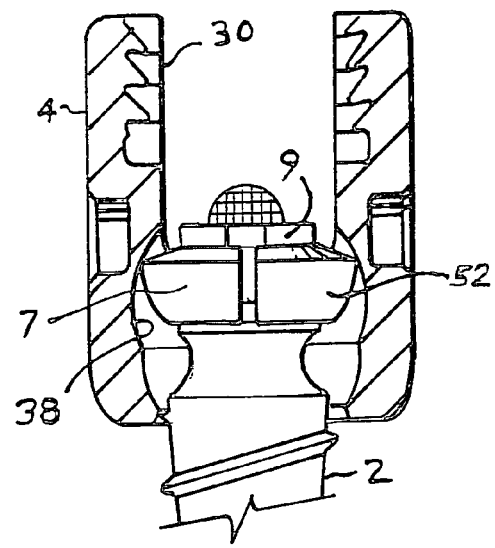
FIG. 6 is a view similar to FIG. 3 and shows the retainer ring positioned on the capture end of the threaded shank.

FIGS. 3-8 illustrate step by step assembly of the components of the bone screw arrangement 1. In FIG. 3, the ring 7 is inserted into the head 4 through the interior of the U-shaped cradle 30. The ring 7 is oriented with its axis at a right angle to the axis of the bore 24 and to the side surfaces 32 of the cradle 30. FIG. 4 illustrates the ring 7 oriented with its axis parallel or coincident with the axis of the bore 24 and neck 26, by rotating the ring 7 within the assembly cavity 38. In FIGS. 5 and 6, the capture end 9 of the shank 2 is inserted through the bore 24 and engaged with the retainer ring 7 so as to snap the ring 7 over the capture end 9. This is accomplished by pressing the shank 2 into the head 4, causing the ring to engage a constriction at the top of the assembly cavity 38. The relative resistance encountered by the ring 7 allows the capture end 9 to expand the circumference of the retainer ring 7, by expansion of the split 48, so that the capture end 9 enters the central bore 50 of the ring 7. The capture end 9 includes a shoulder 56 which limits penetration of the capture end 9 into the retainer ring 7, as shown in FIG. 6.

Figure 7:
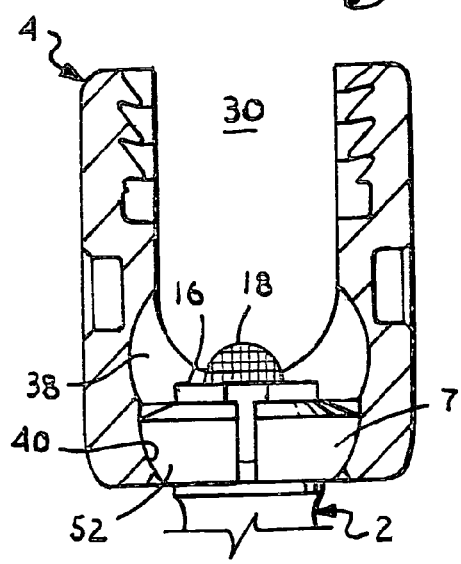
FIG. 7 is a view similar to FIG. 3 and shows the capture end of the shank with the installed retainer ring positioned in a spherical pivot seat of the screw head.
Figure 8:
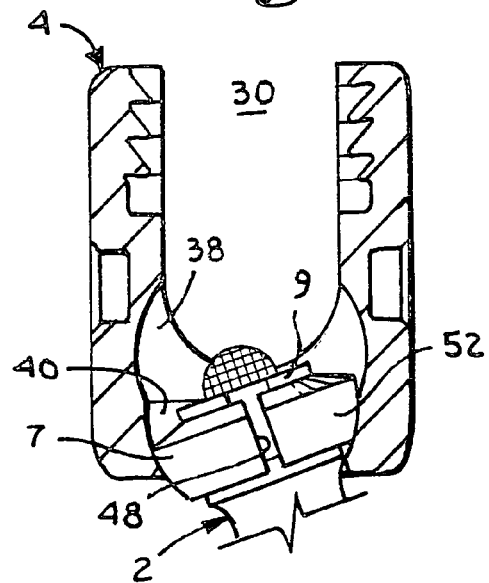
FIG. 8 is a view similar to FIG. 3 and shows the threaded shank with retainer ring pivoted to a selected angle relative to the screw head.

FIG. 7 shows the arrangement 1 with the retainer ring 7 lowered from the assembly position and positioned in the spherical seat 40 and the central axis of the shank 2 coaxial with the central axis of the head 4. FIG. 8 shows the shank 2 angled relative to the head 4. The spherical seat 40 and spherical outer surface 52 of the retainer ring 7, when seated in the seat 40, allows universal angular positioning of the shank 2 relative to the head 4 within a limited range, as is shown in FIG. 8. The retainer ring 7, thus, performs the double functions of preventing the capture end 9 of the shank 2 from slipping through the neck 26 and, in conjunction with the seat 40, forms a ball joint for relative orientation of the shank 2 and head 4.

Under some circumstances, it may be desirable to assemble the shank 2 and head 4, prior to threading the shank 2 into the vertebra 3 or other bone. Thereafter, the shank 2 may be conveniently screwed into the vertebrae 3 by passing the installation tool through the cradle 30 to engage the grooves 14 of the capture end 9. The vertebra 3 may be predrilled with a pilot hole or the like (not shown) to minimize stressing the bone 3. Once the shank 2 has been threaded to its desired depth, the head 4 can be oriented as desired. The rod 5 is positioned in the cradle 30, engaging the knurled dome 18, and the closure plug 10 is advanced into the head 4 to clamp the rod 5 between the capture end 9 and the closure plug 10. When the preset torque limit of the plug 10 is reached, the break-off head 44 separates from the closure plug 10. The force transmitted by torquing of the closure plug 10 transmits through the rod 5 and through the dome 18 to the ring 7. The partial spherical surface 52 of the ring 7 is thereby urged into tight frictional relationship with the partial spherical surface 40 of the head 4, thereby locking the angular configuration of the head 4 relative to the shank 2.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial head bone screw assembly for surgical implantation and comprising:
   (a) a shank having a threaded body and a capture end, the capture end having a top surface;
   (b) a head having a channel outwardly open and adapted to receive a rod within said channel; said head having a shank mating side with a bottom shank receiving bore formed therein, and an inner seating surface; said head having a cavity therein communicating with said bore;
   (c) said capture end of said shank being received within said cavity through said bottom bore of said head;
   (d) a retainer ring with a split therein to enable resilient expansion and contraction of a diameter of said retainer ring; said retainer ring being positioned in said head cavity so as to be able to expand and capture said shank while within said cavity so as to retain said shank capture end within said head; said shank and said retaining ring forming a joined shank and retainer ring structure wherein the top surface of the capture end is located above the retainer ring when the shank the retainer ring are joined, the retainer ring pivotally rotates in combination with said shank on said head seat surface enabling selective angular positioning of said shank with respect to said head, when in an assembly configuration; and
   (e) a closure member operably mountable within said head in such a manner as to close said channel.

2. An assembly as set forth in claim 1 wherein:
   (a) said retainer ring has a substantially radial split to enable resilient expansion and contraction of a diameter of said retainer ring.
3. An assembly as set forth in claim 1 wherein:
   (a) said capture end of said shank has a tool formation adapted to enable engagement by a tool for rotation.
4. An assembly as set forth in claim 1 wherein:
   (a) said head has an internal guide and advancement structure formed therein; and
   (b) said closure member has a radially outward surface with an external guide and advancement structure formed thereon which is sized and shaped to rotatably mate with said internal guide and advancement structure of said head.
5. An assembly as set forth in claim 1 wherein:
   (a) said head has an internal mating structure formed therein; and
   (b) said closure member has a radially outward surface with an external mating structure formed thereon which is configured to rotatably mate with said internal mating structure of said head.
6. In a polyaxial head bone screw assembly for surgical implantation and including a shank having a threaded body and a capture end and a head having an outward opening channel adapted to receive a rod within said channel, said head having a shank receiving bore formed therethrough and a seat, the improvement comprising:
   (a) said capture end of said shank having a top surface, and being received within said shank receiving bore of said head;
   (b) a retainer ring that is loaded separately from said shank into said head and being joined to said capture end of said shank within said head to retain said capture end within said head; said shank and retainer ring forming an assembled structure wherein the top surface of the capture end is located above the retainer ring when the shank and retainer ring are joined, and the assembly structure is rotatable in the head seat so as to enable angular positioning of said shank with respect to said head; said shank and retainer ring being joined such that said retainer ring rotates with said shank during the angular positioning of said shank relative to said head; and
   (c) a closure member operably engageable with said head and adapted to engage a rod within said channel so as to produce friction between said retainer ring and said head seat so as to secure said head from movement relative to such a rod and to secure said head from angular movement relative to said shank and said retainer ring structure, when in a locking configuration.
7. An assembly as set forth in claim 6 wherein:
   (a) said retainer ring has a radial split to enable resilient expansion and contraction of a diameter of said retainer ring.
8. An assembly as set forth in claim 6 wherein:
   (a) said capture end of said shank has a dome formation to enable non-slip engagement with a rod within said channel of said head.
9. An assembly as set forth in claim 6 wherein:
   (a) said capture end of said shank has a knurled dome having a radius and being adapted to enable non-slip engagement with a rod within said channel of said head.
10. An assembly as set forth in claim 6 wherein:
   (a) said capture end of said shank has a tool formation so as to be adapted enable non-slip engagement by a tool.

11. An assembly as set forth in claim 6 wherein:
(a) said head has an internal guide and advancement structure formed therein; and
(b) said closure member has a radially outward surface with an external guide and advancement structure formed thereon which is sized and shaped to rotatably mate with said internal guide and advancement structure of said head.

12. A polyaxial bone screw assembly, comprising:
a) a head including a rod-receiving channel, an inner cavity communicating with the rod-receiving channel and having a seat therein, and lower opening joining the seat with an outer surface of the head;
b) a resilient retainer ring received in the cavity and including an inner bore with an inner surface, and an outer seating surface; and
c) a shank including a threaded body and a capture end extending upwardly therefrom, the capture end having a top surface, the threaded body being adapted for implantation into a bone, and the shank being sized and shaped to be received through the head lower opening and into the cavity;
d) the retainer ring inner bore surface resiliently receiving and matingly engaging the shank capture structure such that the top surface of the capture structure is located above the retainer ring, when the shank is received through the lower opening and joined with the retainer ring, the retainer ring outer seating surface slidingly engaging the head seat, such that the shank polyaxially rotates relative to the head while in an adjustment configuration; and
e) a closure member operably received in the head in such a manner as to capture a rod located within the rod-receiving channel.

13. A polyaxial bone screw assembly for surgical implantation comprising:
a) a shank having a lower threaded body and an upper capture end; the shank capture end having an upper dome that is convex in shape and that has a first radius;
b) a head having a channel for receiving a rod and a cavity for receiving the shank capture end, such that the shank dome extends into the channel; and
c) a retainer that operably joins with and rotates with the shank in the head cavity such that the retainer is located below the upper dome; the retainer being sized and shaped to hold the shank capture end within the cavity and allow polyaxial movement of the shank relative to the head during angular positioning of the shank; the retainer having a second radius at the maximum width of the retainer that is larger than the first radius.

* * * * *